United States Patent [19]

von Hagens

[11] 4,278,701

[45] * Jul. 14, 1981

[54] ANIMAL AND VEGETAL TISSUES PERMANENTLY PRESERVED BY SYNTHETIC RESIN IMPREGNATION

[76] Inventor: Gunther von Hagens, Jahnstr. 6, Heidelberg, Fed. Rep. of Germany, 6900

[ * ] Notice: The portion of the term of this patent subsequent to May 27, 1997, has been disclaimed.

[21] Appl. No.: 92,544

[22] Filed: Nov. 8, 1979

Related U.S. Application Data

[63] Continuation of Ser. No. 851,101, Nov. 14, 1977, Pat. No. 4,205,059.

[30] Foreign Application Priority Data

Mar. 9, 1977 [DE] Fed. Rep. of Germany ....... 2710147
May 7, 1977 [DE] Fed. Rep. of Germany ....... 2720607

[51] Int. Cl.³ ............................................. A01G 5/06
[52] U.S. Cl. ...................................................... 427/4
[58] Field of Search ................. 427/4; 35/20; 156/57; 118/50; 424/3

[56] References Cited

U.S. PATENT DOCUMENTS

| | | | |
|---|---|---|---|
| 2,464,512 | 3/1949 | Joffe | 427/4 |
| 2,658,836 | 11/1953 | Fessenden | 427/4 |
| 2,698,809 | 1/1955 | Fessenden | 427/4 |

*Primary Examiner*—Sam Silverberg

[57] ABSTRACT

A solid, substantially anhydrous body essentially consisting of animal or vegetal tissue and a synthetic resin substantially uniformly distributed in the tissue is prepared from a water-bearing, normally soft tissue, subject to rapid decomposition and loss of weight by evaporation of its water content in air at 20° C., by substantially completely removing the water content while substantially maintaining the original tissue shape and volume, uniformly impregnating the water-free tissue with a fluid precursor composition capable of being polymerized into a solid synthetic resin, and holding the impregnated tissue under polymerization conditions until the precursor composition is cured to a solid resin more rigid than the original tissue.

15 Claims, No Drawings

ANIMAL AND VEGETAL TISSUES PERMANENTLY PRESERVED BY SYNTHETIC RESIN IMPREGNATION

This is a continuation of application Ser. No. 851,101, filed on Nov. 14, 1977 now U.S. Pat. No. 4,205,059.

This invention relates to the preservation of animal and vegetal tissues, and particularly to a method of converting normally soft and putrifiable tissue into a solid body retaining many of the properties of the tissue, and to the resulting product.

Presently available preservation methods convert tissues into objects which retain relatively few properties of the starting material for an extended period and frequently do not permit examination of the preserved tissue material in the same manner in which the fresh tissue may be examined. Storage in antiseptic liquids, encapsulation in blocks of transparent plastics, drying or freeze drying, embedding in paraffin, sealing between plastic sheets, and other methods in present common use do not fully satisfy the need for permanently preserved tissue specimens which may replace fresh tissue for teaching purposes, nor are tissue specimens preserved by conventional methods fully satisfactory for the purposes of forensic medicine.

It is a primary object of this invention permanently to preserve animal and vegetal tissues in such a manner that all relevant properties of the starting material may be retained, the term "animal tissue," as employed in this specification and the appended claims, including human tissue.

More specifically, the invention aims at providing preserved tissues which are capable of being examined by virtually all important optical methods commonly employed in examining fresh tissues.

With these objects and others in view, the invention, in one of its more specific aspects, provides a solid, substantially anhydrous body essentially consisting of animal or vegetal tissue and of a synthetic resin substantially uniformly distributed in the tissue, the tissue, in the absence of the resin, being soft and subject to decomposition, evaporation of its water content, and consequent weight loss when exposed to the atmosphere at ordinary temperature (about 20° C.). In another aspect, the invention provides a method of preparing the aforementioned body in which the water content is substantially completely removed from water-bearing animal or vegetal tissue while the original shape and volume of the tissue is substantially maintained. The resulting water-free tissue is impregnated with a fluid precursor composition capable of being polymerized into a solid, synthetic resin, and the impregnated tissue is held under polymerization conditions until the precursor composition is cured.

The specific nature of the tissue to be preserved is not critical, and I am not aware at this time of any soft vegetal or animal tissue that could not be converted by this invention to a solid body retaining many properties of the fresh tissue, particularly optical properties, yet virtually immune to decay and capable of withstanding substantial mechanical stress. The specific nature of the fluid precursor composition employed as an impregnant is also unimportant within obvious limits. The precursor must not chemically attack the tissue while fluid, and many monomers and prepolymers now commercially available and yet to be discovered meet and will meet this condition. Entirely satisfactory results have been obtained so far with acrylic resins, epoxy resins, polyester resins, polyurethanes, and silicone resins varying widely in their chemical properties and their processing characteristics, particularly in the conditions under which they are formed by polymerization of monomers or intermediates.

While some monomers, such as hydroxyethyl methacrylate, are water soluble, the compatibility with water is lost on polymerization, and it is necessary, therefore, that the tissue to be preserved be stripped of virtually its entire water content prior to impregnation and curing. Yet, the shape and volume of the tissue should not be changed by the dehydration process if the ultimate product is to duplicate the fresh tissue as closely as possible.

If the resin precursor is water-miscible or capable of absorbing water, the water may be removed from animal tissue by perfusion with the precursor. The term perfusion, as employed in this specification and the appended claims, defines the injection of a liquid into vessels permeable to the injected liquid which diffuses into adjacent tissue. Perfusion of the water-bearing tissue with a suitable precursor solution, while feasible, is normally not preferred because of the relatively large amount of costly precursor needed to flush the water content from the fresh tissue. It is an advantage of this method that removal of water and impregnation of the tissue is achieved simultaneously and may be followed directly by heating or other treatment providing polymerization conditions for the precursor.

It is generally less costly to replace the water in fresh animal tissue by sequential immersion of the tissue in repeated changes of organic solvents beginning, for example, with least expensive, aqueous ethanol, and progressing gradually to anhydrous ethanol and/or acetone which may then be followed by other organic solvents to suit processing conditions, that is, solvents which are either compatible with the resin precursor and with the solid resin to be obtained therefrom by polymerization, or which are at least compatible with the precursor and volatilize prior or during curing. Dichloromethane is compatible with most polymerization mixtures and preferred wherever applicable. However, a solvent compatible with the solid, cured resin may be chosen so as not to volatilize during curing of the precursor. The resin in the hard object may then be made porous by removal of the solvent after curing. The water originally present in the tissue may be replaced in part by a gaseous fluid, particularly if it is desired to make the impregnated specimen opaque. The gaseous fluid may be air or residual solvent vapor in porous resin. Carbon dioxide may be distributed in polyurethane resins if traces of residual water in the tissue react with isocyanate in the precursor composition.

The solvent-bearing, but substantially anhydrous tissue may be impregnated with resin precursor by immersion or by perfusion with the fluid precursor composition, and impregnation of the immersed prepared tissue may be hastened by evaporating or otherwise releasing the organic solvent from the tissue, the solvent being chosen to be more volatile than any necessary component of the precursor combination which, in addition to monomer and partly polymerized derivatives thereof, may contain catalysts or hardeners, accelerators, plasticizers, and like conventional ingredients. Exposing the precursor and the object immersed therein to a vacuum usually causes impregnation in a very short time if the solvent is volatile in the vacuum, and the precursor composition is not overly viscous. Compositions up to about 5000 cps have been used without difficulty, and even more viscous compositions may be employed for impregnation by alternating application of negative and positive pressure. Much lower viscosity is necessary for successful impregnation by perfusion.

As will be described in more detail hereinbelow, a wide variety of human and other animal tissues may be converted to durable, solid objects showing all the features of interest in the tissues to the student of anatomy or histology, and the resin impregnation method of the invention may be supplemented with conventional techniques of making tissue cavities more readily visible, as by filling the cavities with materials of contrasting color different from that of the tissue and of the impregnating resin. Entire organs or paper-thin sections may be impregnated according to the invention, and soft plant tissues of every description lend themselves to the same treatment.

If the impregnating resin and the tissue are both transparent and of substantially the same index of refraction, the resin is invisible in the finished product which may be entirely transparent. If excessive impregnant is wiped, drained or otherwise removed from the surface of the impregnated tissue, the tissue may be viewed through a magnifying glass or through a microscope in incident light in the same manner as fresh tissue. Thin, impregnated tissue sections of the invention may be viewed under a microscope in transmitted light, and all details of tissue structure are fully preserved and visible.

Thin tissue sections when impregnated with only enough synthetic resin to occupy the space initially filled with water may be too fragile to be handled, and it is preferred to cover them with a continuous layer of impregnating resin, preferably transparent, which greatly contributes to the strength of the body while not interfering with inspection of the tissue surface under a magnifying glass even when as thick as four millimeters. Continous resin surface layers too thin to be detected by the unaided eye have been found to give surprising strength to an impregnated, thin tissue section.

No significant change in shape or volume of a tissue may occur if it is freeze dried, and water removal by freeze drying may be followed immediately by perfusion with or immersion in a fluid resin precursor composition.

After immersion, excess precursor composition is preferably drained off or removed by wiping and the like before polymerization conditions are established if the surface of the finished product is to duplicate the surface characteristics of the fresh tissue. When polyester or epoxy resins are employed as impregnants, it is advisable to monitor the temperature of the fluid composition to avoid polymerization and a sharp increase in viscosity before excess resin precursor is removed.

Silicone rubber precursor compositions of low viscosity have been found best for producing resilient objects faithfully duplicating the surface configuration of fresh tissue. Their polymerization is not inhibited by oxygen in the atmosphere, but can be retarded as needed by maintaining a low temperature (below 32° F.) during impregnation. Their index of refraction (n=1.405) enhances the natural appearance of the impregnated tissue surface, and the resiliency of the cured silicone rubber simulates the softness of the fresh tissue to some reduced degree.

Polymerization conditions are chosen to suit the specific resin precursor composition employed within limits set by the need to avoid decomposition of the tissue, and may include elevated temperatures, irradiation with ultraviolet light, the presence of initiators or catalysts, and other factors known in themselves. If atmospheric oxygen unduly inhibits the curing of polyester resin impregnant, the impregnated object may be immersed in anhydrous glycerol or held in a nitrogen atmosphere during curing.

The following Examples are further illustrative of this invention. The resin compositions mentioned in the Examples were commercial products whose precise composition was not known and not needed to be known for using the compositions. All proportions and percentage values are by weight unless specifically stated otherwise.

EXAMPLE 1

A human kidney recovered one day after death was perfused by injection with a mixture of 10 liters 0.9% aqueous sodium chloride solution and 10 liters 4% aqueous formaldehyde solution. The arteries thereafter were injected with a silicone rubber solution diluted with 20% toluene and colored red by means of a dissolved dye, and the veins were injected with a similar, blue silicone rubber solution. The kidney then was immersed sequentially in 50% aqueous ethanol, 70% ethanol, 96% ethanol, absolute ethanol, a mixture of equal volumes of alcohol and acetone, and ultimately in absolute acetone, the dwell time in each solution being approximately 1 hour. Substantially the entire water content of the kidney tissue was replaced by volatile organic solvent in this manner.

The kidney so prepared was then immersed in a small vat in a liquid mixture of 80% (vol.) methyl methacrylate and 20% dibutyl phthalate with a 50% solution of benzoyl peroxide in dibutyl phthalate containing 1.5% benzoyl peroxide based on the methacrylate, and a small amount of a commercial amine accelerator. The vat and its contents were placed under a glass bell which was evacuated gradually until no further bubbles of volatile solvent were released by the kidney tissue (about 40 minutes). Rapid evaporation which could have distorted the original appearance of the specimen was avoided by manually controlling the rate at which the pressure under the bell was reduced. The kidney so impregnated was mounted on a dissecting needle and adhering resin precursor solution, which by now had reached a syrupy consistency, was permitted to drain. The mounted kidney hardened in air after about three days, and reached its ultimate hardness in eight days.

One of the kidney poles was cut off. The cut surface showed that the kidney had hardened throughout. Its surface was rough, white to red in color, not glossy, and not translucent. The cortex, medulla, arteries and veins, area cribrosa with proi uriniferi were clearly visible to the naked eye. The medullary rays and glomerula were visible at 10x magnification.

EXAMPLE 2

A rat liver bleached by treatment with 35% hydrogen peroxide for several hours was dehydrated by sequential perfusion with aqueous ethanol solutions of increasing concentration (70%, 80%, 96%, absolute ethanol), followed by a 1:1 mixture of ethanol and acetone, and absolute acetone. A silicone rubber solution of contrasting color was injected into the arteries, and the liver so prepared was immersed in a commercial, heat-curing epoxy resin prepolymer solution and held in a vacuum as described in Example 1. All volatile solvent was expelled within 25 minutes. The impregnated liver then was stored in an oven at 50° C. for four hours until completely hardened.

The product so obtained had a smooth and reflecting surface. It was transparent except for the blood vessels which were clearly seen in transmitted light.

EXAMPLE 3

A globular cactus having a diameter of approximately 15 cm was partly hollowed out from its root end by means of a curette, and it was then immersed sequentially for three hours each in 50% aqueous acetone, pure acetone, and dichloromethane. Thereafter it was immersed in a solution of a commercial epoxy resin prepolymer stable at low temperature, but curing at elevated temperature. The vat holding the prepolymer and the immersed cactus was stored in a vacuum at 10° C. for eight hours, whereby all volatile solvent was extracted. When drained of excess prepolymer and held in an oven at 40° C. for six hours, the cactus hardened, but otherwise retained its original appearance and color.

EXAMPLE 4

A rat was injected intraperitoneally with a solution of 0.1 ml heparin (500 units USP) containing an anesthetic. It was then perfused sequentially with distilled water, a 4% formaldehyde solution, and a mixture of equal volumes of hydroxyethyl methacrylate and methyl methacrylate containing 1% azo-diisopropionic acid dinitrile as a curing catalyst. The plastic precursor was hardened at 50° C.

The chest and abdominal cavity of the rat were opened. All details of the plastic-impregnated anatomical structure were fully preserved including the eyes, the plexus brachialis, the vessels of the mesentery, but also the individual hairs of the fur.

EXAMPLE 5

A piece of human kidney tissue was fixed by immersion in 4% formaldehyde solution, washed in water, and stained with hematoxylin. It was dehydrated in the manner described above by sequential immersion in ethanol of increasing concentration and ultimately in a mixture of acetone and xylene. It was then immersed in a polyester prepolymer solution under vacuum for 30 minutes, drained of excess of resin precursor, and cured at 50° C. in six hours until solid and resilient.

When viewed under a 10X magnifying glass, the glomerula, medullary rays, and inner zone were clearly discernible. When viewed under a stereoscopic microscope at a magnification of 180x, the air-filled tubuli contorti were clearly seen in the kidney surface. When the hardened tissue was broken into two pieces, microscopic features of the kidney structures were clearly recognized in the fracture surface (blood vessels, glomerula, and uriniferous tubules).

EXAMPLE 6

A human kidney was perfused with water and formaldehyde solution as described above, frozen, and cut into slices 0.5 mm thick by means of a rotary cutting machine. A slice was stained with hematoxylin as in Example 5, and colored silicone rubber solution was injected into the blood vessels. It was then dehydrated by sequential immersion in aqueous alcohol of increasing concentration and finally in acetone as described in Example 1. It was thereafter impregnated in a vacuum with a somewhat viscous mixture of 70% methyl methacrylate and 30% dimethylglycol phthalate containing 0.5% benzoyl peroxide, and ultimately permitted to cure in the atmosphere.

Details of the kidney tissue were readily seen by the naked eye or under a magnifying glass.

EXAMPLE 7

A human brain was fixed in aqueous formaldehyde solution for a few hours, frozen, and slices approximately 0.5 mm thick, 13 cm long, and 12 cm wide were prepared by means of a rotary cutting machine. A slice or foil so produced was dehydrated by sequential immersion in alcohol and acetone as described above and impregnated with partly polymerized, but still fluid methyl methacrylate. After curing of the resin, at 50° C. for six hours, basal ganglia, the stem of the cerebellum, the cortex, white matter, and blood vessels were clearly visible.

In impregnating the specimens described in Examples 6 and 7, the fluid polymer precursor was poured into a flat, polyethylene-filled dish in a thin layer. The dehydrated tissue specimen then was placed on the surface of the impregnating mixture and air bubbles trapped under the specimen were removed as far as possible by wiping the exposed specimen surface toward a free edge. When the vat thereafter was placed in a sealed, evacuated container, the solvent evaporated from the exposed surface of the specimen and was replaced by impregnating mixture entering from below.

EXAMPLE 8

A catalyzed epoxy resin prepolymer composition which still had the consistency of a somewhat viscous fluid was poured in a thin layer on a flat, horizontal glass plate, lined with polyethylene foil and was confined laterally by a frame of stainless steel wires. A section of a human lung, 0.5 mm thick, was dehydrated by sequential immersion in water-miscible organic solvents which were ultimately displaced by dichloromethane in a manner obvious from the preceding examples. The lung section was placed carefully on the surface of the epoxy resin composition. At the same rate at which the solvent evaporated from the exposed surface of the lung section, the resin composition permeated the specimen which was heavier than the resin composition and ultimately was immersed in the same after the dichloromethane had been released. The glass plate carrying the embedded lung specimen was stored at 70° C. for two days when the epoxy resin was completely cured. The resin impregnated foil having a thickness of approximately 1 mm was stripped from the glass plate and had adequate mechanical strength to permit handling with no more care than would be required by a sheet of resin.

EXAMPLE 9

A human placenta was dehydrated by sequential immersion in water-miscible organic solvents and ultimately in dichloromethane. It was immersed in a commercial urethane casting resin composition diluted with an approximately equal volume of N, N-dimethylformamide. After the immersed placenta had been exposed to a vacuum at ambient temperature for 15 minutes, the dichloromethane was completely replaced by the casting resin solution, but virtually none of the dimethylformamide had evaporated. Excess resin composition was permitted to drain from the impregnated placenta, and it was then held at 50° C. to complete curing of the resin while sealed in a small glass vessel which prevented evaporation of the diluent before curing was completed. Ultimately the cured object was held in a vacuum at 80° C. until the dimethylformamide was released.

Although the cured casting resin had an index of refraction not significantly different from that of the impregnated tissue, the surface structure of the tissue was clearly evident because of the incomplete, though uniform impregnation. Evaporation of the dimethylformamide had left the plastic porous. Yet, the tissue had not shrunk. The amount of plastic in the tissue was too small to be capable of detection by means of a stereoscopic microscope at 100x magnification. The volume of the plastic was smaller than that of the pres in the same which were filled with a gaseous fluid include residual solvent vapor and carbon dioxide formed by reaction of isocyanate in the resin precursor with traces of water in the tissue.

EXAMPLE 10

A rat was prepared for plastic impregnation in the manner described in Example 1 and dehydrated by sequential immersion in 50%, 70%, 96% ethanol, a 1:1 mixture of ethanol and acetone, and ultimately dichloromethane. It was then perfused with an epoxy resin prepolymer composition capable of thermal curing which was diluted with one fifth of its weight of dichloromethane. An excess of the resin solution was permitted to drain off, and the impregnated rat was cured at 50° C. while sealed in a glass vessel preventing escape of the solvent. The impregnating resin was not visible to the naked eye after curing and subsequent volatilization of the dichloromethane.

EXAMPLE 11

A human stomach, recovered one day after death, was immersed in 10 liters 10% formaldehyde solution containing approximately one teaspoon sodium nitrite and one teaspoon ascorbic acid for a few hours. It was then dehydrated by sequential immersion in four aqueous acetone solutions ranging in acetone concentration from 60% to 90% and ultimately in 100% acetone. Each of the acetone solutions and the pure acetone contained ascorbic acid in about the same proportion as the formaldehyde solution. Immersion time was about one week in each of the five liquids, and exposure to light was held to a minimum to avoid decomposition of the ascorbic acid.

The practically water-free stomach removed from the acetone was immersed in dichloromethane for several weeks to displace the acetone. The specimen recovered much of its original color during this period and was thereafter immersed in a commercial silicone rubber prepolymer contained in a vat. A glass plate was placed over the specimen to keep it submerged. The vat was covered with a bell jar, and the jar with its contents was placed in a refrigerator at about 4° C. to retard curing of the rubber and permit saturation of the stomach tissue with the impregnating composition while the dichloromethane was removed by gradually evacuating the jar to 5 mm Hg over a period of four hours, the rate of evacuation being controlled in such a manner that a steady, but gentle stream of solvent vapor bubbles was released by the specimen.

The specimen then was removed from the silicone composition, and adhering excess composition was permitted to drain off. The specimen was suspended from a filament in an oven controlled at 95° C. After three hours, its surface was cleaned of residual, partly cured silicone rubber with an artist's brush dipped in dichloromethane, and curing was continued for a total of 24 hours. The impregnated and cured specimen had a light pink color. Its surface configuration was not visibly different from that of the stomach as freshly removed from the corpse. It could be cut into very thin sections at temperatures low enough to harden the elastomeric impregnating agent, and the sections showed the characteristic texture of the stomach wall.

The specimen was subjected to a simulated aging test in which it was held in air for six weeks at 90° C. No changes in mechanical and optical properties were observed. While more rigid than the original stomach tissue, the impregnated specimen was flexible and resilient enough to permit inspection of all portions of the mucous membrane without permanent deformation.

The silicone rubber compositions employed in the preceding Examples were transparent when cured, but they had an index of refraction too low to make specimens impregnated therewith transparent in sections exceeding a few millimeters. It is an oustanding advantage of silicone rubber compositions that they undergo minimal shrinkage, if any, during curing, a shrinkage of 1% being the greatest observed so far.

Silicone rubber compositions which cure at room temperature are commercially available and may be employed for impregnating specimens whose tissue is readily permeable to the uncured composition within the short time available. An initial viscosity of about 800 cps is maintained for about eight hours at 0° C. Various grades of thermally curing silicone rubber compositions are available and permit impregnation of specimens not suitable for treatment with grades of the composition lacking an adequate polymerization period.

Acrylic resin precursors generally cure exothermally, and careful temperature control is necessary during curing of specimens impregnated therewith. Practically transparent specimens are readily obtained because the index of refraction of this class of resins is close to that of many tissues.

The prepolymer solutions from which polyurethanes are formed by curing are particularly low in viscosity. They are conveniently injected into vessels, particularly blood vessels in animal tissues, and quickly permeate the tissue surrounding the vessels.

The specimens successfully impregnated by the method of this invention to date range in size up to a human arm with fingers and shoulder attached, and no human tissue not capable of being preserved by the method of this invention is known to me. The method is of relatively minor importance in the preservation of bones, wood, and similar relatively hard animal and plant tissue containing little, if any water, and therefore not subject to weight loss and shrinkage by water evaporation, nor to rapid decomposition by putrefaction or other decomposition when exposed to the atmosphere at normal temperatures of about 20° C.

Surface layers of cured resin are sometimes permissible where the layer is thin, at most 4 mm, and follows the contour of the underlying tissue. A resin layer covering at least a portion of the tissue surface is desirable with tissue specimens too thin to withstand careless handling even when impregnated.

It should be understood, of course, that the foregoing disclosure relates only to preferred embodiments, and that it is intended to cover all changes and modifications of the examples of the invention herein chosen for the purpose of the disclosure which do not constitute departures from the spirit and scope of the invention set forth in the appended claims.

What is claimed is:

1. A method of preparing a body consisting essentially of anhydrous animal or vegetal tissue and a water-insoluble synthetic resin substantially uniformly distributed in said tissue which comprises:
    (a) replacing the water content of a water-bearing body of animal or vegetal tissue with an organic solvent volatile in a vacuum;
    (b) holding said body bearing said solvent in contact with a fluid precursor composition in a vacuum until said solvent is volatilized and replaced in said body by said composition, said composition being capable of being polymerized into a solid, water-insoluble synthetic resin;
    (c) removing adhering precursor composition from the surface of said body; and
    (d) holding said body under polymerization conditions until said precursor composition in said body is cured to said solid resin.

2. The method of claim 1 wherein the viscosity of said composition during said removing is not higher than 5000 cps.

3. The method of claim 1 wherein said body bearing said solvent is held in contact with said precursor composition by immersing the body in said composition.

4. The method of claim 1 wherein said tissue is an animal tissue including a vessel accessible to a hollow needle and permeable to said composition, said body being held in contact with said composition by injecting said composition into said vessel.

5. The method of claim 1 wherein said solid resin is a silicone rubber.

6. A method of preparing a body consisting essentially of anhydrous animal or vegetal tissue and a water-insoluble synthetic resin substantially uniformly distributed in said tissue which comprises:
    (a) replacing the water content of a water-bearing body of animal or vegetal tissue with an organic solvent volatile in a vacuum;
    (b) holding said body bearing said solvent in contact with a fluid precursor composition in a vacuum until said solvent is volatilized and replaced in said body by said composition, said composition being capable of being polymerized into a solid, water-insoluble, synthetic resin; and
    (c) holding said body under polymerization conditions until said precursor composition in said body is cured to said solid resin.

7. The method of claim 6 wherein the viscosity of said composition during said holding in contact is not higher than 5000 cps.

8. The method of claim 6 wherein said body bearing said solvent is held in contact with said precursor composition by immersing the body in said composition.

9. The method of claim 6 wherein said tissue is an animal tissue including a vessel accessible to a hollow needle and permeable to said composition, said body being held in contact with said composition by injecting said composition into said vessel.

10. The method of claim 6 wherein said vessel is a blood vessel.

11. The method of claim 6 wherein said solid resin is a silicone rubber.

12. The method of claim 6 wherein the amounts of said solvent being volatilized and of said composition being held in contact with said body are such that said composition is substantially completely absorbed and uniformly distributed in said body.

13. The method of claim 6 wherein said volatile organic solvent is dichloromethane.

14. A method of preparing a body consisting essentially of anhydrous animal or vegetal tissue and a water-insoluble synthetic resin substantially uniformly distributed in said tissue which comprises:
    (a) replacing the water content of a water-bearing body of animal or vegetal tissue with an organic solvent volatile in a vacuum;
    (b) holding said body bearing said solvent in contact with a fluid precursor composition in a vacuum until said solvent is volatilized and replaced in said body by said composition, said composition being capable of being polymerized into a solid, water-insoluble, synthetic resin;
    (c) removing adhering precursor composition from the surface of said body; and
    (d) holding the body under polymerization conditions until said precursor composition in said body is cured to said solid resin,
wherein said precursor composition includes another organic solvent substantially non-volatile in said vacuum and under said polymerization conditions, said other organic solvent being removed from said body after said curing.

15. A method of preparing a body consisting essentially of anhydrous animal or vegetal tissue and a water-insoluble synthetic resin substantially uniformly distributed in said tissue which comprises:
    (a) replacing the water content of a water-bearing body of animal or vegetal tissue with an organic solvent volatile in a vacuum;
    (b) holding said body bearing said solvent in contact with a fluid precursor composition in a vacuum and at said temperature until said solvent is volatilized and replaced in said body by said composition, said composition being capable of being polymerized into a solid, water-insoluble, synthetic resin; and
    (c) holding said body under polymerization conditions until said precursor composition in said body is cured to said solid resin,
wherein said precursor composition includes another organic solvent substantially non-volatile in said vacuum and under said polymerization conditions, said other organic solvent being removed from said body after said curing.

* * * * *